United States Patent
Baginski

(10) Patent No.: US 8,883,232 B2
(45) Date of Patent: Nov. 11, 2014

(54) HORSE FEED AND TREATMENT METHODS

(76) Inventor: Debra Baginski, Westminster, MD (US)

( * ) Notice: Subject to any disclaimer, the term of this patent is extended or adjusted under 35 U.S.C. 154(b) by 913 days.

(21) Appl. No.: 12/454,267

(22) Filed: May 14, 2009

(65) Prior Publication Data

US 2010/0021430 A1 Jan. 28, 2010

Related U.S. Application Data

(63) Continuation-in-part of application No. 12/379,418, filed on Feb. 20, 2009, now abandoned.

(60) Provisional application No. 61/064,174, filed on Feb. 20, 2008.

(51) Int. Cl.
| | |
|---|---|
| *A23K 1/18* | (2006.01) |
| *A23K 3/00* | (2006.01) |
| *A23L 1/30* | (2006.01) |
| *A23C 9/00* | (2006.01) |
| *A23K 1/00* | (2006.01) |

(52) U.S. Cl.
USPC .................. 426/2; 426/54; 426/73; 426/585; 426/623

(58) Field of Classification Search
USPC ................................................ 426/2, 54, 623
See application file for complete search history.

(56) References Cited

PUBLICATIONS

Basic Horse Nutrition. Available online at www.uky.edu on Feb. 1, 2001.*
Kronfeld, et al., Equine Syndrome X, the Metabolic Disease, and Equine Grain-Associated Disorder. Journal of Equine Veterinary Science, vol. 23, No. 12 pp. 567-569 (Dec. 2003).*
Delobel, et al., Linseed Oil Supplementation in Diet for Horses: Effects on Palatability and Digestibility. Livestock Science 116 (208) 15-21. Available online on Sep. 19, 2007.*

* cited by examiner

*Primary Examiner* — Rena Dye
*Assistant Examiner* — Assaf Zilbering
(74) *Attorney, Agent, or Firm* — Andrew C. Aitken

(57) ABSTRACT

A horse feed mixture and method of treating a horse is disclosed. Feed mixtures disclosed contains more than 15% spelt, vegetable oil and vitamins and have less than 20% by weight fillers and less than 5% by weight sugar. The feed may be used to treat ailments including underweight condition, founder, colic, obesity, ulcers, inflammation, and chronic disease.

7 Claims, No Drawings

HORSE FEED AND TREATMENT METHODS

This is a continuation-in-part of U.S. application Ser. No. 12/379,418. The Applicant claims of the benefit of the filing date of U.S. Provisional Application No. 61,064,174 entitled "Improved Horse Feed" that was filed on Feb. 20, 2008 and U.S. application Ser. No. 12/379,418, entitled "Horse Feed and Methods of Treating Horses" filed Feb. 20, 2009. The present disclosure relates to improved feeds that are appropriate for horses and the use of these feeds to treat horses.

BACKGROUND

Spelt (*Triticum spelta*) is a hexaploid species of wheat that is not grown in large quantities in the U.S. or Europe compared to conventional wheat crops. While spelt has recently found a new market as a health food, it is not widely available in commercial quantities. Spelt is sometimes considered a subspecies of common wheat (*T. aestivum*), in which case its botanical name is considered to be *Triticum aestivum* subsp. *spelta*. While spelt resembles common wheat, the grain is a bit longer and more pointed. Spelt is planted in the fall of the year, maturing the following summer. In the U.S., spelt has been primarily grown in Ohio. The widespread commercial production of spelt has been abandoned in favor of production of more modern varieties of wheat that, in general, have a higher yield, a shorter growing season and have better resistance to disease. Spelt has been used for both human consumption and also as an animal feed.

Spelt contains approximately 15-21% protein, which is higher than conventional commercially grown wheat. It also has higher levels of complex carbohydrates, iron, potassium and the B vitamins than conventional wheat. Spelt has been reported to be easier to digest than other wheat products because of its higher solubility in water. Spelt also contains nutrients that aid in blood clotting and it is believed to stimulate the immune system. Due to spelt's high water solubility and relatively fragile gluten, the grain's vital substances can be absorbed quickly with a minimum of digestive work.

Currently, there is not a wide selection of commercially available horse feeds that horse owners may select for their animals. Horse feeds that are presently marketed in the U.S. typically contain fillers such as processed grain by-products and roughage, as well as forage products, molasses or molasses by-product, plant protein products, grain, and vegetable oils such as soybean oil. Processed grain by-products include grain remnants, empty grain hulls, brewers dried grains, distillers dried grains, corn gluten, wheat millings and wheat bran. Conventional forage products may include alfalfa meal and grass hay. Molasses is added to horse feeds primarily to improve the palatability of the feed. Molasses or by-products of molasses is often added to feed to disguise dirt and other contamination and improve the appearance of the product. Molasses that is used in feeds may be from sugar beet or cane molasses.

Roughage products referred to herein means apple products, barley hulls, beet pulp, oat hulls, peanut hulls and rice hulls. Plant protein products used in conventional feed include cottonseed meal, linseed meal, soybean meal, soybeans and yeast. The grain products used in conventional feeds are barley, corn, oats, wheat, rice and rye. In general, horse feeds are used to supplement grazing, particularly when a horse is racing or is undergoing other strenuous activity. Feed supplements such as hay, grain by-products and roughage and forage do not have high caloric value compared to grains.

In connection with prior art horse feed products, an adult horse may eat as much as approximately 12 lbs. of feed per day, which includes a substantial amount of grain by-product, roughage and sugar content. The administration of this volume of feed with high sugar content results in slower metabolic response by the horse, and the horse's liver becomes overloaded with processing of sugars. In addition, in view of the high amounts of non-nutritional by-products and roughage in conventional feeds, more volume is fed to the horse in order to achieve the proper amount of nutrients. As a result, the digestive processing of the feed is slow, which results in feed remaining in the small and large intestine for longer periods of time. When feed remains in the horse's digestive system for longer periods of time, the incidence of inflammation, colic, and chronic disease are increased. In addition, the feed in the digestive system begins to ferment.

The soy oil or other oils used in commercially available feeds is typically not cold pressed and contains detergents to increase shelf life. Commercially available feeds also contain roughage products to add to the fiber content. In addition, many commercially available feeds also contain ingredients such as mineral oil and corn oil. However, because mineral oil and corn oil are hydrogenated, horses cannot break down these types of oils.

The purpose of carbohydrates in the equine diet is to provide energy. Grains and fiber are considered complex carbohydrates and are slow to release nutritional components during the digestion process. Complex carbohydrates help slow down the release of sugar. Simple carbohydrates are quickly processed and provide immediate energy to the animal. Complex carbohydrates are processed more slowly and help to sustain energy.

The amount of food that an equine stomach can hold is related to the type of feed given. Conventional feeds typically include considerable by-product, and are provided in pellet form. These feeds are lighter and contain fewer calories per pound than a condensed feed and consequently, must be provided in larger quantities. A problem with such lighter feed is that the volume of feed that a horse can actually digest in a given time period is limited. If a horse is not able to digest the appropriate amount, then the amount of nutrition that the horse is receiving is reduced.

A horse's gastric capacity is limited, so feeding the horse frequently, 3 times per day for example, will most likely to assist and improve its digestion rate. However, many horse owners are not willing or able to feed their horses more than twice a day.

SUMMARY

The Applicant has found that the incorporation of spelt, and the presence of fillers at amounts less than 20% by weight or less, and the presence of sugar at amounts less than 5% by weight or less, results in a horse feed that results in improved health to horses and also positively correlates with improved weight gain. The term filler as used herein means roughage and grain by-products. The use of spelt as a significant component of the horse feed and the presence of sugars at less than 5% by weight, and the presence of fillers at less than 20% by weight is believed to provide benefits to the health of the animal. These benefits are best for older horses, horses that have been sick, or any horse that is suffering from nutritional deficiencies. In other embodiments, the feed has less than 10% by weight fillers. In another embodiment, the feed has less than 5% by weight fillers. In another embodiment no fillers are added to the feed. In other embodiments, a feed has less than 3% by weight sugars. In another embodiment, no sugar is added. Sugar used herein means raw sugar, processed sugar, molasses and molasses by-product.

The horse feed that is disclosed herein can be described as a condensed feed, which distinguishes it from most commercially available horse feeds. In this regard, the feed is a concentrated product does not contain substantial amounts of non-nutritional supplements with low caloric value. The disclosed feed is considered to be condensed because it contains less than 20% by weight fillers. A further feed disclosed has less than 10% by weight fillers. An additional feed disclosed has less than 5% fillers. An additional embodiment of the feed has no fillers. While the examples provided herein disclose a feed with no fillers, the Applicant contemplates that feed may contain up to 20% of such fillers and still provide beneficial effects. It is believed that the use spelt as a major component of the feed contributes to the beneficial effects of the feeds that are disclosed. Embodiment of the feeds with less than 20% by weight filler and which also includes vitamins and a blend of vegetable oil that is not hydrogenated, can provide less feed volume to the horse while allowing the horse's digestive system to efficiently process the feed without stress to the major organ systems. Concentrated feed is heavier and requires a smaller quantity.

DETAILED DESCRIPTION

The feed disclosed is intended to help the horse digest the amount of nutrients necessary and assist with the clearing of excess food. Using the disclosed feed, the horse will not be weighed down by undigested parts of the feed. In addition, using the feed mixtures disclosed in the examples, the horse's liver is not taxed because less 5% by weight sugar is added. In other embodiments less than 3% by weight sugar is added. In another embodiment no sugar is added. As discussed above, fillers include empty hulls of grain or other items without substantial caloric content that have been substituted for fiber. A feed that is disclosed contains necessary ingredients and contains such fillers in an amount of less than 20% by weight of the feed. In another embodiment a feed contains less than 10% by weight filler. In other embodiments, the feed contains less than 5% by weight fillers. In other embodiments, no fillers are added to the feed mixture.

The term fillers as used herein refers to processed grain by-products, brewers dried grains, distillers dried grains, corn gluten feed, wheat millings and bran (rice and wheat) and roughage. Roughage means apple products (dried), barley hulls, beet pulp (dried), and hulls (oat, peanut and rice). The term forage products includes alfalfa meal (dehydrated or sun-cured), grass hay, lespedeza meal and other vegetation. The term molasses products as used herein includes beet and cane molasses, distilled molasses and dried soluble molasses. The term plant protein products includes cottonseed meal, linseed meal, soybean meal, soybeans (heat processed), and yeast (cultured). Grain products includes barley, corn, oats, wheat, rice and rye. In addition, spelt is considered a grain product. These materials include farinaceous material and thus include wheat, wheat flour, and wheat meal by-products.

The vitamin premix may include beneficial probiotics, digestive enzymes and other vitamins that are conventionally used in horse feed. The following materials may be included in a vitamin premix:

*Lactobacillus acidophilus* ("*L. acidophilus*"), *Bifidobacterium* and *Enterococcus faecium* ("*E. faecium*") bacteria can be collectively referred to as health-promoting or beneficial bacteria for many reasons suggested by research studies. Each of these species can be found in both the small and large intestines. *L. acidophilus* is an important type of beneficial bacteria found in the digestive tract, primarily found in the small intestine, and can turn milk sugar into lactic acid. *L. acidophilus* and *E. faecium* tend to be more active in the small intestine, while *Bifidobacterium* is primarily found in the large intestine. *E. faecium* aids in the movement of food through the digestive tract. Another probiotic, *Aspergillus niger*, is cultured and used in connection with extraction of the enzymes glucose oxidase (GO) and alpha-galactosidase (AGS). *Trichoderma longibrachiatum*, assists in pH balancing of the digestive tract due to environment related stressors. *Bacillus subtilis* is a proteolytic enzyme and hydrolysis starch. *Bifidobacterium longum* is primarily found in the large intestine, is important for B vitamin production and is thought to inhibit the action of harmful enzymes. *Lactobacillus casei* is thought to reduce diarrhea in horses and appears to modify the digestive microflora and enhance the immune system during its transit through the digestive tract. *Lactobacillus plantarum* is believed to decrease abdominal bloating. Animal research has shown that it decreases translocation and improves mucosal and liver status. It also improves the immunological status of mucosa and reduces mucosal inflammation. *Pediococcus acidilacticii* is believed to improve gastrointestinal tract health by reducing the level of pathogenic bacteria present, and also provides probiotic assistance by extending shelf life of food product. Such probiotics or combinations of one or more of these pro-biotics, may be added to the vitamin premix in conventional amounts.

The health-promoting bacteria that are identified above may attach to the villi lining of the horse's small intestine to improve nutrient absorption. The attachment or colonization by beneficial bacteria prevents harmful bacteria from attaching and increasing in numbers. Many health-promoting bacteria are also lactic acid-producing bacteria and assist in maintaining a stable digestive tract pH to restrict *E. coli* and salmonella growth. Beneficial bacteria may produce bacteriocins and other metabolites to restrict *E. coli* and salmonella growth. Health-promoting bacteria may also enhance a horse's immune function. The enhancement of the immune function could be a result of increased nutrient absorption to support the immune system. Another theory is that immune receptors recognize the beneficial bacteria in the digestive tract and are triggered to increase activity.

Digestive enzymes, amino acids and other components that may be present in the vitamin premix may also include amylase, protease, cellulase, lysine, tryptophane, glycine, cystine, arginine, and tyrosine. The vitamin premix may also contain calcium, calcium carbonate, potassium sulfate, magnesium sulfate, monocalcium phosphate, dicalcium phosphate, niacin, folic acid, phosphor, magnesium, potassium, sulfur, iron, zinc, manganese, copper, cobalt, iodine, selenium, biotin, and/or chelated minerals. The vitamin premix in an embodiment contains alfalfa, kelp, vitamin A, vitamin E, vitamin B-12, vitamin C, vitamin D3, D-biotin, vitamin B6, vitamin B3, vitamin K, iron proteinate, yeast, riboflavin, thiamine mononitrate, colbalt proteinate, and d-calcium pantothenic acid. Vitamin premixes designed to be used in connection with horse feeds are commercially available.

Chelated minerals may be provided in the horse feed so the digestive system does not need to work as hard to break down the minerals. An amino-acid on a chelated mineral may link with the complementary amino-acid in the digestive tract, and, if the body is deficient in a particular amino acid, it may become temporarily re-balanced using a chelated mineral.

In embodiments, the feed lacks or substantially lacks artificial ingredients. Artificial ingredients may include genetically engineered grains, and anything that is man-made, including synthetic vitamins.

In embodiments, the components of the feed mix are organic. Used herein the term "organic" means that no herbicides are sprayed on the grains in the field or in the bins used to store the grain. In embodiments, the grains are roasted.

A low level or even the absence of sugars is helpful in connection with feeding horses that are on antibiotics. Horses on antibiotics and that have high levels of sugars in their diet may result in an environment that is *Candia Albican* friendly and can cause growth of fungus in the body. Further, digestion is slowed with the presence of sugars or molasses in the feed because the material can ferment in the large and small intestines. Such fermentation can cause inflammation and stagnation throughout the alimentary canal and interfere with digestion.

Embodiments of the feed mixtures have a low amount of grain by-products and roughage, components that substantially lack caloric value, compared to some commercially available feeds. This feature is believed to have a beneficial effect on the horse. When undigested food or filler product is allowed to remain in the intestine, a horse can have allergic reactions, colic, liver congestion, kidney problems and/or suffer from sinus problems, sinus ulcers and other health problems.

In embodiments no or little corn (less than 5%) is present in the feed. Corn is avoided in such embodiments because it may cause an increased phosphorus ratio in the gut, causing acidity. An increase in acidity is to be avoided, especially in connection with horses that have a history of stomach ulcers. Such horses will react poorly to feeds with corn as one of the primary ingredients. The addition of corn in feed also increases the possibility of ulcers, inflammation and fluid retention.

Some or all of the grain used in the feed may be roasted before the vitamin premix and oils are added. Spelt and barley may be roasted while oats are not roasted. The feed examples disclosed below may include grain mixtures with or without roasting. Roasting has a number of advantages including that its use is a natural form of pest control. Roasting also balances protein and makes for higher digestibility because the grain is easier to break open when chewed. Oats are very hardy, so it is not as important to roast them.

The selection of spelt for the feed is advantageous because it requires less feed than wheat or other grains to achieve the same nutritional results, per pound of horse. Spelt also has low allergen content, thereby reducing inflammation in the stomach and further reducing the incidence of stomach ulcers and inflammatory type illnesses.

Example 1

A horse feed is made from a mixture of the following components: a grain product mixture containing 33% spelt, 45% barley and 22% oats, a dehydrogenated vegetable oil, and a vitamin premix. The dehydrogenated vegetable oil (or in the alternative an oil that is not hydrogenated) is present in an amount that equals approximately 6 gallons per 2000 lbs. of feed. The vitamin premix is comprised of vitamins, minerals and pro-biotic bacteria and digestive enzymes and is added in an amount equaling approximately between 1% and 1.5% of the weight of the grain product mixture.

In this example, the grain product has the following characteristics: a crude protein minimum is approximately 11.8%; the crude fat minimum is approximately 5.4%; the crude fiber minimum is approximately 3.1% and the maximum is 9%. This example uses a minimum of approximately 6 gallons of soy/flax oil in 2000 lbs. of feed. In Example 1, one gallon of soy/flax oil blend has 102 oz. of soy oil and 26 oz. of flax oil. Other blends of soy and flax oils may also be beneficial, including ranges from 10% to 90% soy oil with respect to other vegetable oils, and 10% to 90% flax oil with respect to other vegetable oils. In embodiments the vegetable oil is cold pressed and not hydrogenated. Cold pressed oil is oil which has been produced with the use of a low heat technique. The introduction of heat to the process of making oil will degrade the flavor, nutritional value, and color of the oil. Heat, however, increases the yield. The term "cold pressed oil" is subject to different regulations, depending on the part of the world in which it is made. In the European Union, for example, oil which is labeled as cold pressed must be produced in an environment which never exceeds a certain temperature. The temperature varies, depending on the oil, but is generally around 80 degrees Fahrenheit (27 degrees Celsius). As used herein, the term "cold pressed" is intended to mean a product made in conformance with European Union regulations governing the term. In embodiments of the invention, the vitamin premix contains vitamins, digestive enzymes, pro-biotics, kelp and alfalfa. In embodiments the vitamin premix is added to the grain in an amount of 400 lbs to every 35,000 lbs of grain and therefore the vitamin premix accounts for approximately 1.14% of the weight of the feed mixture before the addition of vegetable oils.

The feed of Example 1 may be contrasted with prior art commercially available horse feeds that have a higher fiber content due to the existence of grain by-product and roughage. The presence of grain by-product is one of the reasons that most grain companies recommend more weight of feed per pound of horse than is recommended by the Applicant in connection with the feed that is disclosed.

The feed of Example 1 is fed to a horse based on approximately 1.5 lbs. of feed per 500 pounds of horse per day, divided into two feedings. According to another embodiment, a feed according to Example 1 is administered 1.25 lbs. of feed per 500 lbs. of horse per day, divided into two feedings. According to another embodiment, the feed according to Example 1 is administered 2 lbs. of feed per 500 lbs of horse per day, divided into two feedings. According to another embodiment, the feed according to Example 1 is administered at a daily rate of 0.5 lbs of feed per 500 lbs of horse per day, divided into two feedings. According to another embodiment, the feed according to Example 1 is administered at a daily rate of 0.25 lbs of feed per 500 lbs of horse per day, divided into two feedings. In these examples, the horse may be pastured and allowed to graze and may consume as much forage as the horse would naturally eat. In contrast, commercially available feed products on the market generally recommend approximately 6-9 lbs. of feed per 600 lbs. of horse, per day.

In the examples disclosed below, the amount of feed administered to the horse is approximately 1.5 lbs. per 500 lbs. of horse per day or, the amount administered is approximately 0.5 lbs per 500 lbs of horse per day. This amount may be altered depending on the condition of the horse and, for example, may range from 0.25 lbs. to 4.5 lbs. per 500 lbs or horse per day. In embodiments, the feed is administered or made available to the horse at least twice daily.

Example 2

A horse feed is made from a mixture of the following components: a grain product containing 100% spelt, a blend of soy oil and flax oil, and a vitamin premix. The blend of soy oil and flax oil is added at an amount that equals approximately 6 gallons per 2000 lbs. of feed. The vitamin premix is comprised of vitamins, minerals, digestive enzymes and probiotic bacteria and is added at an amount equaling approximately between 1% and 1.5% of the weight of the grain product mixture.

Example 3

A horse feed is made from a mixture of the following components: a grain product containing 100% roasted spelt, a blend of soy oil and flax oil, and a vitamin premix. The blend of soy oil and flax oil is added at an amount that equals approximately 6 gallons per 2000 lbs. of feed. The vitamin premix is comprised of vitamins, minerals, enzymes and pro-biotic bacteria and is added at an amount equaling approximately between 1% and 1.5% of the weight of the grain product mixture.

Example 4

A horse feed is made from a mixture of the following components: a grain product containing 15% spelt 15% barley and 70% oats; soy oil; and a vitamin premix. The soy oil is added at an amount that equals approximately 6 gallons per 2000 lbs. of feed. The vitamin premix is comprised of vitamins, minerals, enzymes and pro-biotic bacteria and is added at an amount equaling approximately between 1% and 1.5% of the weight of the grain product mixture.

Example 5

A horse feed is made from a mixture of the following components: a grain product containing 50% spelt 25% barley and 25% oats; soy oil; and a vitamin premix. The soy oil is added in an amount that equals approximately 6 gallons per 2000 lbs. of feed. The vitamin premix is comprised of vitamins, minerals, enzymes and pro-biotic bacteria and is added in an amount equaling approximately between 1% and 1.5% of the weight of the grain product mixture.

Example 6

A horse feed is made from a mixture of the following components: a grain product containing 65% spelt, 20% barley and 15% oats; a blend of soy and flax oil; and a vitamin premix. The blend of soy oil and flax oil is added in an amount that equals approximately 6 gallons per 2000 lbs. of feed. The vitamin premix is comprised of vitamins, minerals, enzymes and pro-biotic bacteria which is added in an amount equaling approximately between 1% and 1.5% of the weight of the grain product mixture.

Example 7

A horse feed is made from a mixture of the following components: a grain product containing 90% spelt, 5% Barley and 5% oats; a blend of soy and flax oil; and a vitamin premix, wherein the blend of soy oil and flax oil is added at an amount that equals approximately 6 gallons per 2000 lbs. of feed and the vitamin premix is comprised of vitamins, minerals, pro-biotic bacteria and enzymes which is added at an amount equaling approximately between 1% and 1.5% of the weight of the grain product mixture.

The oils used in the examples recited are added in amounts of approximately 6 gallons per 2000 lbs. of feed. In the examples that refer to soy and flax blends, one gallon of the soy and flax oil blend has 102 oz. of soy oil and 26 oz. of flax oil. In these examples the vitamin premix is added to the grain at a blend ratio of approximately 30 lbs. of vitamin premix to 2000 lbs. of grain.

A useful vitamin premix is available for sale from Gooseberry Natural Feed, LLC of Westminster, Md. As used herein the term vitamin premix includes vitamins and minerals at the minimum. In embodiments the vitamin premix also includes digestive enzymes and pro-biotic bacteria.

While the feed examples include vegetable oils and vitamin premix, and the use of the oils and vitamin premix is preferred, it is contemplated that the feed may be sold without these components. In this regard, it is important to recognize the absence of substantial amounts of fillers provides beneficial effects. As illustrated herein, the grain component includes examples wherein spelt is employed at ratios from 15% to 100% with the respect to the other grains used in the feed. The protein fat and fiber ratios are dependent upon the grains being roasted or plain, plus the addition of ingredients. The measurements provided for spelt, oats, barley ratio are by weight. Each of the examples is also characterized by the substantial absence of sugars and grain by-products.

The feed examples discussed above may be to treat a variety of conditions as demonstrated by the following examples.

Example 8

According to an embodiment of treatment methods, the feed mixture recited in Example 1 is fed to an undernourished mature horse to treat the horse and increase the weight of the horse. The feed is fed to the horse at approximately 1.5 lbs. per 500 lbs. of horse per day. In this method, the horse is permitted to graze and the feed is administered to the horse twice daily.

Example 9

According to an embodiment of treatment methods, the feed mixture recited in Example 1 is fed to a mature horse to prevent colic in a horse that has a history of colic. The feed is fed to the horse at 1.5 lbs. per 500 lbs. of horse per day. This feed is provided in addition to allowing the horse to graze and the feed is administered twice daily.

Example 10

According to a further treatment method, the feed mixture set forth in Example 1 is fed to a horse having ulcers to treat the ulcers. The feed is fed to the horse at approximately 1.5 lbs. per 500 lbs. of horse per day. The feed is provided in addition to allowing the horse to graze and the feed is administered twice daily.

Example 11

According to a further treatment method, the feed mixture set forth in Example 1 is fed to a horse having allergies to mitigate the problems with allergies. The feed is fed to the horse at approximately 1.5 lbs. per 500 lbs. of horse per day. The feed is provided in addition to allowing the horse to graze and the feed is administered twice daily.

Example 12

According to a further method, the recipe of the first example is fed to a horse having founder to mitigate the symptoms of founder. The feed is fed to the horse at approximately 1.5 lbs. per 500 pounds of horse per day. This feed is may be provided in addition to allowing the horse to graze. The feed is preferably administered at least twice daily.

Example 13

According to a further method, the recipe of the first example is fed to an obese horse. The feed mixture is fed to the horse at 1.5 pounds per 500 pounds of horse per day. The feed is administered at least twice daily.

Example 14

According to a further method, the recipe of the first example is fed to a horse having founder or metabolic problems to treat said conditions. The feed is fed to the horse at 1.5 pounds per 500 pounds of horse per day. This feed is may be provided in addition to allowing the horse to graze. The feed is administered at least twice daily.

Example 15

According to an embodiment of treatment methods, the feed mixture recited in Example 1 is fed to an undernourished mature horse to treat the horse and increase the weight of the horse. The feed is fed to the horse at a rate of approximately 0.5 lbs. per 500 lbs. of horse per day. In this method, the horse is permitted to graze and the feed is administered to the horse twice daily.

Example 16

According to an embodiment of treatment methods, the feed mixture recited in Example 1 is fed to a mature horse to prevent colic to a horse that has a history of colic. The feed is fed to the horse at a rate of approximately 0.5 lbs. per 500 lbs. of horse per day. This feed is provided in addition to allowing the horse to graze and the feed is administered twice daily.

Example 17

According to a further treatment method, the feed mixture set forth in Example 1 is fed to a horse having ulcers to treat the ulcers. The feed is fed to the horse at a rate of approximately 0.5 lbs. per 500 lbs. of horse per day. The feed is provided in addition to allowing the horse to graze and the feed is administered twice daily.

Example 18

According to a further treatment method, the feed mixture set forth in Example 1 is fed to a horse having allergies to mitigate the problems with allergies. The feed is fed to the horse at a rate of approximately 0.5 lbs. per 500 lbs. of horse per day. The feed is provided in addition to allowing the horse to graze and the feed is administered twice daily.

Example 19

According to a further method, the recipe of the first example is fed to a horse having founder to mitigate the symptoms of founder. The feed is fed to the horse at a rate of approximately 0.5 lbs. per 500 pounds of horse per day. This feed is may be provided in addition to allowing the horse to graze. The feed is preferably administered at least twice daily.

Example 20

According to a further method, the recipe of the first example is fed to an obese horse. The feed mixture is fed to the horse at a rate of approximately 0.5 pounds per 500 pounds of horse per day. The feed is administered at least twice daily.

Example 21

According to a further method, the recipe of the first example is fed to a horse having founder or metabolic problems to treat said conditions. The feed is fed to the horse at a rate of approximately 0.5 pounds per 500 pounds of horse per day. This feed is may be provided in addition to allowing the horse to graze. The feed is administered at least twice daily.

Example 22

According to a further method, the recipe of the first example is fed to a healthy horse. The feed is fed to the horse at a rate of approximately 0.25 pounds per 500 pounds of horse per day. This feed is may be provided in addition to allowing the horse to graze. The feed is administered at least twice daily.

In further embodiments, the recipe according to Example 1 may be administered as follows: to mini horses that weight between 100-300 lbs at a rate of approximately 0.5 lbs per day; to ponies that weigh between 300-500 lbs at a rate of approximately 0.5 lbs per day; to ponies that weight between 500-700 lbs at a rate of approximately 0.75 lbs per day; to horses that weight between 800-1000 lbs at a rate of approximately 1.0 lbs per day; to horses that weight between 1000-1500 lbs at a rate of approximately 1.5 lbs per day; to horses that weight between 1500-200 lbs at a rate of approximately 2 lbs per day.

While a preferred rate of feed according to the recipe disclosed in Example 1 is 0.5 lbs per 500 pounds of horse per day, it is contemplated that feed rates between 0.25 lbs. and 2.0 lbs. per 500 pounds of horse per day would be beneficial depending on the condition of the particular horse, the level of exercise of the horse and the time of year.

The spelt component of the improved recipe may range from 15% of the grain component up to 100% of the grain component (by weight) and still provide many of the benefits that are disclosed herein.

Based upon initial studies of horses that have been administered the feed disclosed in Example 1, the Applicant believes that the feed of example is beneficial to treat conditions including obesity, colic, cushings, arthritis, founder, cancer, metabolic problems, digestion conditions, heart problems, allergies, hoof problems, and underweight issues.

In embodiment of the method of treatment, the feed of examples 1-7 is used to treat conditions including obesity, colic, cushings, arthritis, founder, cancer, metabolic problems, digestion conditions, heart problems, allergies, hoof problems, underweight issues and other horse ailments.

The final feed mixture should have smooth texture and a nutty scent. If a particular horse has an allergy to oats, the oats should be eliminated from the feed in favor of alternative grains such as barley, wheat, rice and rye barley. As referred to above, corn is not preferred.

During winter months or when a horse is in training, the amount of feed provided to the horse should be increased. When starting the horse on the feed examples disclosed, new feed may be mixed with existing feed and the animal caretaker may slowly increase the administration of the new feed and reduce the amount of previously used feed over a 5-to-10 day period to allow the horse to slowly transition to the new feed.

A further advantage of the embodiments of the feeds disclosed herein is that they may be less expensive than conventional feed, at current grain prices. Further, since the examples recited above are concentrated feeds that have less than 20% filler be weight, the feed takes up less space and is easer to ship, store and handle.

Examples 15 through 22 disclose a feed regimen that is particularly beneficial to a horse because it results in a condition where the ingested feed is substantially completely digested and absorbed and the feed does not reside in the alimentary canal compared with conventional feeds that are administered at conventional rates. The use the feed according to the invention and administering the feed at the rates recommended in Examples 15-22 results in very little undigested portions of the feed remaining in the alimentary canal of the horse for a significant time. In contrast, prior art feed and feeding regimens use a less dense feed and the feeding regiments designed for these feeds use significantly more volume of feed per day than that recommended with the feed according to the invention. For example, some prior art feed is administered at rates where an adult horse are fed more than 2.0 lbs. per 500 lbs. of horse per day.

As discussed above, many of the conventional prior art feeds include fillers or non-caloric materials, and as a result, the digestion process takes longer because the horse's digestive system must work to try to break down these materials. Consequently, both nutritional and non-nutritional feed material is left undigested in the horse's gut. Undigested materials that remain in the gut begin to ferment which creates alcohol and gas. This alcohol and gas may contribute to health problems for the horse including colic, an inability to process sugar and overall systemic congestion. The use of the feed and feeding regimens according to the invention reduces or eliminates hindgut fermentation because substantially all of the feed is digested by the horse.

While the use of a concentrated feed such as that disclosed herein or other pure grain feed regimens results in high non-structural carbohydrate levels (NSC) in the diet. For example, for a feed that is substantially comprised of crimped oats, the NSC values would be greater than 50%. A feed products that was substantially all corn would have an NSC level of over 70%. High NSC values are generally believed to be problematic and can contribute to adverse health problems to horses. One way to decrease the NSC value of a feed is to add non-nutritional by-products to the feed. However, as discussed above, the addition of such by-products creates ancillary problems because the horse is then required to eat substantially more volume of feed in order to obtain sufficient nutritional values. Consequently, these feeds require the horse's digestion system to working harder and, material that is not timely digested begins to ferment.

Table 1 provides the average sugar, starch and non-structural carbohydrates (NSC) values for selected feedstuffs.

TABLE 1

| Feedstuff | Sugar | Starch | NSC |
|---|---|---|---|
| Oat hay | 16.0 | 6.3% | 22.1% |
| Barley hay | 14.9 | 5.8% | 20.4% |
| Alfalfa hay | 8.9% | 2.5% | 11.3% |
| Bermudagrass hay | 7.5% | 6.1% | 13.6% |
| Grass hay | 11.1% | 2.9% | 13.8% |

TABLE 1-continued

| Feedstuff | Sugar | Starch | NSC |
|---|---|---|---|
| Alfalfa pellets | 7.2% | 2.3% | 9.3% |
| Alfalfa cubes | 8.3% | 2.0% | 10.2% |
| Grass pasture | 10.3% | 3.4% | 12.1% |
| Rice bran | 6.2% | 17.7% | 21.2% |
| Oats | 4.8% | 44.4% | 54.1% |
| Corn | 3.7% | 70.3% | 73.3% |
| Barley | 6.0% | 53.7% | 61.7% |
| Beet pulp | 10.7% | 1.4% | 12.3% |
| Wheat bran | 8.7% | 23.0% | 30.8% |
| Soybean hulls | 4.3% | 1.9% | 6.3% |
| Wheat middlings | 10.1% | 26.2% | 32.0% |
| Soybean meal | 14.3% | 2.1% | 16.2% |

As the chart demonstrates, oats, corn and barley, and to a lesser extent, wheat bran and wheat middlings, have relatively high levels of both starch and NSC as compared to the values of the other feedstuffs that have been conventionally used as components of horse feed.

In order to mitigate the problems from high NSC and starch levels, the feed according to embodiments of the invention also uses a vitamin premix with includes digestive enzymes and other components as described above which help breakdown both NSC and natural sugars from concentrated grain. Consequently, the feed according to embodiments of the invention, which has a relatively a high NSC level due to its use of high concentration of grain, is balanced with enzymes, vitamins and mineral supplements.

It will be understood that the embodiments described herein are merely exemplary and that a person skilled in the art may make many variations and modifications without departing from the spirit and scope of the invention. All such variations and modifications are intended to be included within the scope of the invention.

I claim:

1. A method of feeding a horse comprising: feeding the horse a feed mixture comprising: a grain product, vegetable oil and a vitamin premix, and wherein said grain product comprises at least 15% by weight spelt, and said feed mixture comprises less than 20% by weight filler, and said feed mixture comprises less than 5% by weight sugar and said vegetable oil is added to said feed mixture at a rate of approximately 6 gallons per 2000 lbs of feed.

2. The method of feeding a horse recited in claim 1 wherein said feed mixture comprises no sugar by weight.

3. The method of feeding a horse recited in claim 1 wherein said feed mixture comprises less than 10% by weight filler.

4. The method of feeding a horse recited in claim 1 wherein said feed mixture comprises less than 5% by weight filler.

5. The method of feeding a horse as recited in claim 1 wherein when said vegetable oil comprises dehydrogenated vegetable oil.

6. The method of feeding a horse as recited in claim 5 wherein said dehydrogenated vegetable oil comprises a blend of soy oil and flax oil.

7. The method of feeding a horse as recited in claim 1 wherein the feed is administered a total daily rate of approximately 1.5 pounds of feed per 500 pounds of horse per day.

* * * * *